US009777021B2

(12) United States Patent
Delferro et al.

(10) Patent No.: US 9,777,021 B2
(45) Date of Patent: Oct. 3, 2017

(54) LUBRICANT ADDITIVES

(71) Applicant: Qatar Foundation, Doha (QA)

(72) Inventors: Massimiliano Delferro, Chicago, IL (US); Tobin J. Marks, Evanston, IL (US); Q. Jane Wang, Mount Prospect, IL (US); Yip-Wah Chung, Wilmette, IL (US); Hassan S. Bazzi, Doha (QA); Afif M. Seyam, Doha (QA); Michael Desanker, Evanston, IL (US); Blake Johnson, Chicago, IL (US); Danni Jin, Mountain View, CA (US)

(73) Assignee: Qatar Foundation, Doha (QA)

( * ) Notice: Subject to any disclaimer, the term of this patent is extended or adjusted under 35 U.S.C. 154(b) by 0 days.

(21) Appl. No.: 15/013,878

(22) Filed: Feb. 2, 2016

(65) Prior Publication Data
US 2017/0217993 A1 Aug. 3, 2017

Related U.S. Application Data

(60) Provisional application No. 62/290,236, filed on Feb. 2, 2016.

(51) Int. Cl.
C10M 133/44 (2006.01)
C07F 1/00 (2006.01)

(52) U.S. Cl.
CPC ............ *C07F 1/005* (2013.01); *C10M 133/44* (2013.01)

(58) Field of Classification Search
CPC .................................................. C10M 133/44
See application file for complete search history.

(56) References Cited

U.S. PATENT DOCUMENTS 2,261,047 A 10/1941 Asseff
2007/0267959 A1 11/2007 Ragini et al.
2010/0044693 A1* 2/2010 Enomoto ............. C07D 231/12
257/40

FOREIGN PATENT DOCUMENTS

| CN | 102504913 A | 6/2012 |
| CN | 104212546 A | 12/2014 |
| CN | 104277887 A | 1/2015 |
| JP | 2006-228939 | 8/2006 |
| WO | WO 03/033629 A1 | 4/2003 |

OTHER PUBLICATIONS

Baoyu et al., "Study of Anti-Contact Fatigue Performance of Lubricant with Nano Silver Particles," Lubrication Engineering, No. 5 (Serial No. 165), with translation, Sep. 2004, 8 pgs.
Wagner et al., "Handbook of X-ray Photoelectron Spectroscopy," Physical Electronics, Eden Prairie, MN, 1979.
Archard, "Contact and Rubbing of Flat Surfaces," Journal of Applied Physics, vol. 24, No. 8, pp. 981-988, Aug. 1953, 9 pgs.

(Continued)

*Primary Examiner* — Taiwo Oladapo
(74) *Attorney, Agent, or Firm* — Martin & Ferraro, LLP

(57) ABSTRACT

Lubricant additives useful as friction reducing additives are disclosed herein that have a structure according to general formula I, where M is metal such as Ag, Au, Zn or Cu, and $R_1$, $R_2$, and $R_3$, are each a hydrogen, or an alkyl, a substituted alkyl, or an aryl group.

27 Claims, 13 Drawing Sheets

(56) References Cited

OTHER PUBLICATIONS

Baraket et al., "Mechanical and tribological properties of CrN/Ag and CrSiN/Ag nanoscale multilayers," Surface & Coatings Technology 204 (2010) pp. 2386-2391, Jan. 14, 2010, 6 pgs.
Bassanetti et al., "Synthesis and Characterization of Silver(I) Pyrazolylmethylpyridine Complexes and Their Implementation as Metallic Silver Thin Film Precursors," American Chemical Society (ACS) Publications, Inorganic Chemistry, 2014, 53(9), pp. 4629-4638, Apr. 18, 2014, 10 pgs.
Burla et al., "SIR2004: an improved tool for crystal structure determination and refinement," Journal of Applied Crystallography (2005), 38, pp. 381-388, Mar. 2005, 8 pgs.
Erck, "Effect of Film Adhesion on Tribological Properties of Silver-Coated Alumina," Surface and Coatings Technology, 43/44 (1990), pp. 577-587, Dec. 10, 1990, 11 pgs.
Farrugia, "WinGX suite for small-molecule single-crystal crystallography," Computer Program Abstracts, Journal of Applied Crystallography (1999), 32, pp. 837-838, Apr. 1999, 2 pgs.
Hsu et al., "Mechano-chemical model: reaction temperatures in a concentrated contact," Wear, 175 (1994), pp. 209-218, Jun. 1994, 10 pgs.
Inman et al., "Microscopy of glazed layers formed during high temperature sliding wear at 750° C.," Wear 254 (2003), pp. 461-467, Mar. 2003, 7 pgs.
Kariniemi, "Plasma-Enhanced Atomic Layer Deposition of Silver Thin Films," American Chemical Society (ACS) Publications, Chemistry of Materials (2011), 23, pp. 2901-2907, May 10, 2011, 7 pgs.
Kawamura et al., "Antiwear Property of Lubricant Additives for High Silicon Aluminium Alloy under Boundary Lubricating Conditions," Wear, 89 (1983) pp. 99-105, Aug. 1, 1983, 7 pgs.
Khorramian et al., "Review of antiwear additives for crankcase oils," Wear, 169 (1993), pp. 87-95, Sep. 1993, 9 pgs.
Lahouij et al., "In Situ TEM Observation of the Behavior of an Individual Fullerene-Like MoS2 Nanoparticle in a Dynamic Contact," Tribology Letters (2011) 42:133-140, Feb. 4, 2011, 8 pgs.
Lai et al., "Kinetic study of the degradation of lubricating motor oil by liquid chromatography and photoacoustic spectrometry," Fresenius Journal of Analytical Chemistry (1993) 347:417-422, Oct. 1993, 6 pgs.
Li et al., "Surface-modification in situ of nano-SiO2 and its structure and tribological properties," Applied Surface Science 252 (2006) 7856-7861, Sep. 15, 2006, 6 pgs.
Lyu et al., "Synthesis of Ag2O Nanocrystals with Systematic Shape Evolution from Cubic to Hexapod Structures and Their Surface Properties," Chemistry A European Journal 2010, 16, 14167-14174, Oct. 19, 2010, 8 pgs.
Ma et al., "Effect of Ag nanoparticles additive on the tribological behavior of multialkylated cyclopentanes (MACs)," Wear 266 (2009) 627-631, Mar. 25, 2009, 5 pgs.
Macrae et al., "Mercury: visualization and analysis of crystal structures," Journal of Applied Crystallography (2006). 39, 453-457, May 2006, 5 pgs.
Mak et al., "Atomic-scale friction measurements on silver and chemisorbed oxygen surfaces," Thin Solid Films 253 (1994) 190-193, Dec. 15, 1994, 4 pgs.
McCain et al., "Tris(phosphino)borato Silver(I) Complexes as Precursors for Metallic Silver Aerosol-Assisted Chemical Vapor Deposition," Inorganic Chemistry, vol. 47, No. 7, 2534-2542, Apr. 7, 2008, 9 pgs.

Mulligan et al., "Ag transport in CrN—Ag nanocomposite coatings," Thin Solid Films 520 (2012) 6774-6779, Sep. 1, 2012, 6 pgs.
Priest et al., "Automobile engine tribology—approaching the surface," Wear 241 (2000) 193-203, Jul. 31, 2000, 11 pgs.
Qi et al., "The tribological performance of selected solid lubricant films in sand-dust environments," Wear 271 (2011) 899-910, Jun. 22, 2011, 12 pgs.
Ren et al., "Plasto-Elastohydrodynamic Lubrication (PEHL) in Point Contacts," Transactions of the ASME, Journal of Tribology vol. 132, pp. 031501-1-11, Jul. 2010, 11 pgs.
Scharf et al., "Solid lubricants: a review," Journal of Materials Science (2013) 48:511-531, Jan. 2013, 21 pgs.
Sliney, "Solid lubricant materials for high temperatures—a review," Tribology International 15(5):303-315, Oct. 1982, 13 pgs.
Spikes, "Mixed Lubrication—an Overview," Lubrication Science 9-3, (9) 221-253, May 1997, 33 pgs.
Sun et al., "Synthesis and characterization of DDP coated Ag nanoparticles," Materials Science and Engineering a 379 (2004) 378-383, Aug. 15, 2004, 6 pgs.
Sun et al., "Synthesis and Tribology Properties of Stearate-Coated Ag Nanoparticles," Tribology Transactions, 53: 174-178, Jan. 2010, 6 pgs.
Tung et al., "Automotive tribology overview of current advances and challenges for the future," Tribology International 37 (2004) 517-536, Jul. 2004, 20 pgs.
Twist et al., "Molecularly-Engineered Lubricants: Synthesis, Activation, and Tribological Characterization of Silver Complexes as Lubricant Additives," Advanced Engineering Materials 2012, 14, No. 1-2, pp. 101-105, Feb. 2012, 5 pgs.
Twist et al., "Silver-Organic Oil Additive for High-Temperature Applications," Tribology Letters, vol. 52, Issue 2, pp. 261-269, Nov. 2013, 9 pgs.
Wang et al., "Tribochemistry and antiwear mechanism of organic-inorganic nanoparticles as lubricant additives," Tribology Letters, vol. 22, No. 1, pp. 79-84, Apr. 2006, 6 pgs.
Yang et al., "Silver Surface Iodination for Enhancing the Conductivity of Conductive Composites," Advanced Functional Materials, 2010, 20, 2580-2587, Jul. 6, 2010, 8 pgs.
Bhushan, "Introduction to Tribology," Second Edition, John Wiley & Sons Inc., Apr. 2013, 721 pgs.
Pawlak, "Tribochemistry of Lubricating Oils," Elsevier: Amsterdam London, Dec. 2, 2003, 371 pgs.
Rudnick, "Lubricant Additives: Chemistry and Applications," CRC Press: 2010, 702 pgs.
Seyam et al., "Synthesis and Characterization of Trimeric Silver(I) 3,5-dimethyl-4-n-amylpyrazolate Complex and its Implication in Tribology," Abstract, INOR-193, 248th ACS National Meeting & Exposition, San Francisco, CA, US, Aug. 10-14, 2014, 2 pgs.
Seyam et al., "Synthesis and Characterization of Trimeric Silver(I) 3,5-dimethyl-4-n-amylpyrazolate Complex and its Implication in Tribology," Abstract, INOR-586, 250th ACS National Meeting & Exposition, Boston, MA, US, Aug. 16-20, 2015, 2 pgs.
Communication relating to the results of the partial international search for PCT/GB2017/050236 mailed on Apr. 3, 2017, 8 pgs.
Desanker, Michael et al., "Oil-Soluble Silver-Organic Molecule for in Situ Deposition of Lubricious Metallic Silver at High Temperatures," ACS Applied Materials and Interfaces, vol. 8, No. 21, Jun. 1, 2016, pp. 13637-13645, 10 pgs.
Woodall, Christopher et al., "Tunable Trimers: Using Temperature and Pressure to Control Luminescent Emission in Gold(I) Pyrazolate-Based Trimers," Chemistry—A European Journal, vol. 20, No. 51, Oct. 21, 2015, pp. 16933-16942, 10 pgs.

\* cited by examiner

LUBRICANT ADDITIVES

The present application claims benefit of Provisional Application No. 62/290,236, filed Feb. 2, 2016; which is incorporated by reference herein.

BACKGROUND OF THE INVENTION

Description of Invention

The present invention relates to lubricant additives. The present invention also relates to methods of forming the lubricant additives. Furthermore, the present invention relates to the use of the lubricant additives.

Background

There is a continuous need for improved engine performance and reduced emissions.

Lubricating oils and greases are engineered to function over a broad range of temperatures and loading conditions. Modern engines operate at higher temperatures, speeds and pressures than previous engines, and therefore require lubricants capable of handling these harsher conditions. Reliable performance in extreme conditions is also necessary in emergency and combat situations.

In automotive engines, the temperature at the surfaces of critical tribological components can easily reach 200° C., while asperity contacts can generate 'flash temperatures' up to 1000° C. of microsecond durations. The extreme pressure and temperature in the contact zones can lead to plastic deformation, wear away mating surfaces, and catalyze undesirable chemical reactions which damage the surfaces and lubricants.

Conventional lubricants and oils undergo degradation via three main pathways: scission, thermolysis, and oxidation. The high temperatures and pressures of typical engines create an environment that is hostile to the long molecular hydrocarbon chains found in lubricants. These degradation pathways lead to irreversible reductions in viscosity and the generation of oil-insoluble acids and salts that corrode surfaces and form performance-damaging sludges. The additive packages used in modern lubricants contain compounds designed to preserve the longevity of the lubricant. These include friction modifiers, viscosity modifiers, dispersants, corrosion inhibitors, and anti-oxidants.

Solid lubricants, applied either as a surface coating or as a lubricant additive, are well-suited for high-temperature operation. Most solid lubricants, such as graphite and molybdenum disulfide, have a strong 2D lamellar structure and weak intracrystalline interactions, enabling low-friction sliding of basal planes under shearing forces.

The ductility of soft metals can also be utilized in lubrication. The low shear-strength of metallic films can form a smooth "glaze layer" on tribosurfaces that lubricates sliding contact, and the low reactivity of noble metals enables this mechanism to function at extreme temperatures.

Silver coatings in contact surfaces have demonstrated friction and wear improvement in temperatures ranging from 25-750° C. Silver nanoparticles have also been shown to greatly increase surface fatigue life, decrease friction and wear, and work synergistically with other lubricant additives. However, silver nanoparticles are costly to produce, difficult to suspend in oil, and often require a surfactant to prevent the particles from agglomerating.

An alternative method for the delivery of lubricious silver is to use a silver-containing molecular precursor. These molecules are designed to undergo thermolysis at elevated temperatures, depositing a layer of metallic silver on mechanical surfaces.

In previous work, three generations of silver precursor molecules were evaluated for their performance as extreme temperature additives in motor oil. The Gen-I additive (FIG. 1a) was used to grow low-resistivity metallic silver thin films by aerosol-assisted chemical vapor deposition (AACVD), while the Gen-II additive (FIG. 1b) exhibited promising wear reduction in fully formulated (military grade 15W40) engine oil at ~200° C. However, it contains phosphorus (P) and sulfur (S) atoms which can poison automotive catalytic converters. The Gen-III additive (FIG. 1c) is a pyrazole-pyridine complex that has the advantage of being P- and S-free, making it benign for use in automotive exhaust systems. However, it requires high wt % loadings (>20%) for effective silver wear and friction reduction, and requires added dimethylsulfoxide (DMSO) for adequate solubility in base oil.

Lower precursor loadings are desirable to reduce the required silver, ensure better solubility, and to accommodate other additives in the additive package. The additive package generally constitutes 10-15% of the entire lubricant formulation. A silver additive that can achieve equal or superior functionality at lower loadings will be necessary to meet the requirements of modern automotive systems.

The present invention seeks to address the problems identified above.

SUMMARY

Lubricant additives are disclosed herein that have the structure of general formula I:

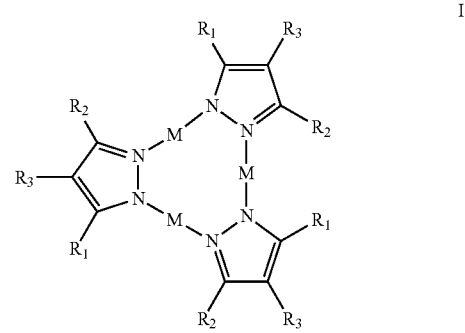

wherein:
  M is a metal,
  $R_1$ is hydrogen, alkyl, substituted alkyl, or aryl,
  $R_2$ is hydrogen, alkyl, substituted alkyl, or aryl, and,
  $R_3$ is hydrogen, alkyl, substituted alkyl, or aryl.

In all aspects, M is Ag, Au, Zn or Cu, preferably M is Ag. But, when M is Ag, $R_3$ is not $(CH_2)_4CH_3$ or $C_6H_{13}$. $R_1$, $R_2$, and $R_3$ may be alkyls, each being independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms. Suitable example alkyls include methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl and eicosyl. If the alkyl is a substituted alkyl, it may be independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms substituted with 1, 2, 3, 4, 5, 6, 7, 8, 9, 10, 11, 12, 13, 14, 15, 16, 17, 18, 19, 20 or more substituents, the substituents independently selected from the group consisting of H, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide,pyrazolo, oxazole, isoxazole, pyridinyl, pyrimidinyl, quinoline, isoquinoline, $SR_4$, $SOR_4$, $SO_2R_4$, $CO_2R_4$, $COR_4$, $CONR_4R_4$, $CSNR_4R_4$ and $SOnNR_4R_4$, where n is zero, one or two, wherein $R_4$ is alkyl or substituted alkyl.

In one variation of the lubricant additives, $R_1$ and $R_2$ are each independently any one of $CH_3$, $CF_3$, t-Bu or $CH_2CH_3$, and may be the same. For example, $R_1$ and $R_2$ are $CH_3$. In addition or independently, $R_3$ is H or $(CH_2)_nCH_3$, wherein n is 0, 1, 2, 3, 4, 5, 6, 7, 8, 9, 10, 11, 12, 13, 14, 15, 16, 17, 18, 19 or 20. In one aspect, $R_3$ is $(CH_2)_5CH_3$.

Mixtures of lubricant additives with oil are disclosed herein. The oil may be motor oil, such as, PAO4 or 15W40 oil.

Methods of forming the lubricant additives discussed above are also disclosed.

The method includes reacting a compound of general formula II:

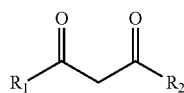

II with a compound of general formula III:

III which may be carried out under basic conditions and/or in acetone in the presence of $K_2CO_3$. Then, the product of the reaction of general formula II and general formula III is reacted with $N_2H_4.H_2O$, which may be carried out in MeOH, to form a nitrogen heterocycle. Then, the nitrogen heterocycle is reacted with a metal oxide, which may be carried out in MeOH. When M is Ag, the metal oxide is $Ag_2O$.

BRIEF DESCRIPTION OF THE DRAWINGS

Embodiments of the invention are described below with reference to the accompanying drawing, in which.

DETAILED DESCRIPTION

The following explanations of terms and methods are provided to better describe the present compounds and methods, and to guide those of ordinary skill in the art in the practice of the present disclosure. It is also to be understood that the terminology used in the disclosure is for the purpose of describing particular embodiments and examples only and is not intended to be limiting.

"Optional" or "optionally" means that the subsequently described event or circumstance can but need not occur, and that the description includes instances where said event or circumstance occurs and instances where it does not.

"Alkyl" refers to straight-chain or branched-chain hydrocarbons having 1, 2, 3, 4, 5, 6, 7, 8, 9, 10, 11, 12, 13, 14, 15, 16, 17, 18, 19 or 20 carbon atoms linked exclusively by single bonds and not having any cyclic structure. Optionally, alkyl includes methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl and eicosyl.

"Aryl" refers to substituted or unsubstituted aromatic hydrocarbons with a conjugated cyclic molecular ring structure of 3, 4, 5, 6, 7, 8, 9, 10, 11 or 12 carbon atoms. Optionally, aryl includes monocyclic, bicyclic or polycyclic rings. Optionally, aryl includes one to three additional ring structures selected from the group consisting of a cycloalkyl, a cycloalkenyl, a heterocycloalkyl, a heterocycloalkenyl, or a heteroaryl. Optionally, aryl includes phenyl (benzenyl), thiophenyl, indolyl, naphthyl, totyl, xylyl, anthracenyl, phenanthryl, azulenyl, biphenyl, naphthalenyl, 1-methylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl. Optionally, aryl refers to aryls substituted with 1, 2, 3, 4 or 5 substituents selected from the group consisting of H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide,pyrazolo, oxazole, isoxazole, pyridinyl, pyrimidinyl, quinoline, isoquinoline, $SR'''$, $SOR'''$, $SO_2R'''$, $CO_2R'''$, $COR'''$, $CONR'''R'''$, $CSNR'''R'''$ and $SOnNR'''R'''$, wherein $R'''$ is alkyl or substituted alkyl.

Figure 1:
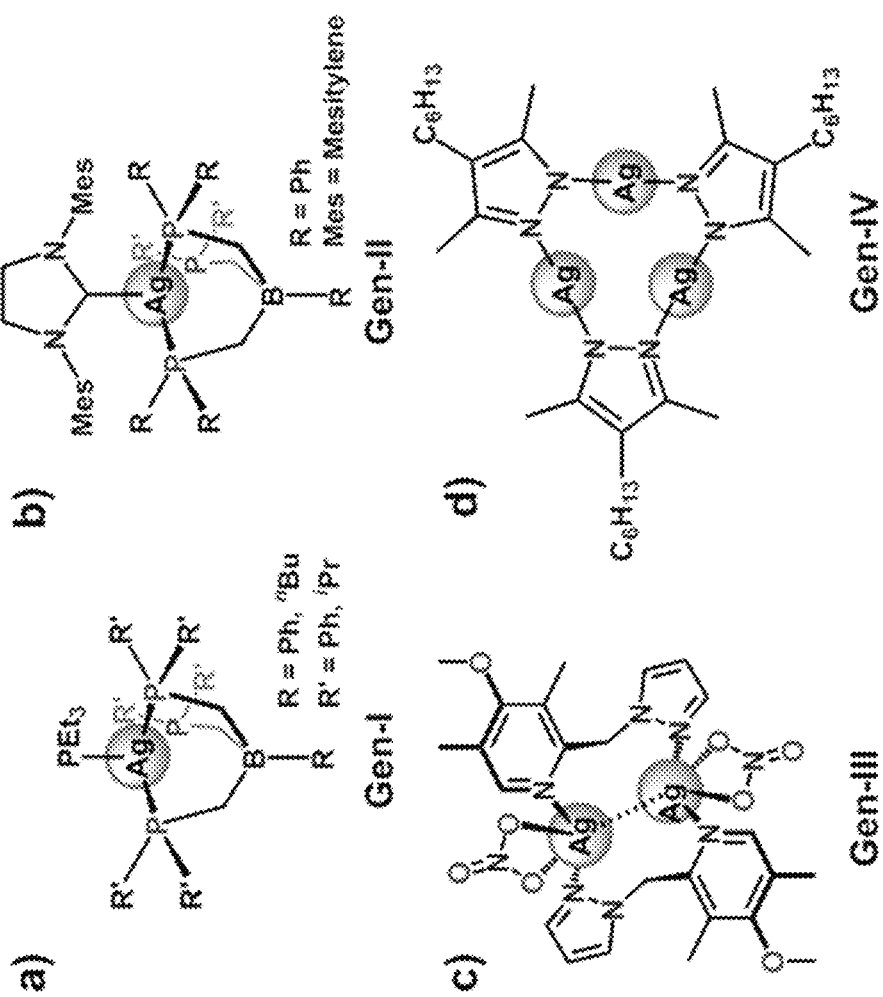
FIG. 1 shows: (a-c) molecular structures of organo-silver lubricant additives known in the art; and, (d) molecular structure an organo-silver lubricant additive 1 according to one aspect of the present invention.

According to one non-limiting embodiment of the present invention, there is provided a P- and S-free trinuclear silver-pyrazole complex bearing $C_6$ alkyl chains (organosilver lubricant additive 1) (FIG. 1d) to enhance oil solubility, which is able to achieve noteworthy wear and friction reduction at high temperatures and at low additive loadings (2.5 wt %). This complex has been synthesized, fully characterized, and tribologically evaluated in PAO4 and fully formulated military grade (15W40) engine oils.

EXPERIMENTAL SECTION

Materials

Silver (I) oxide, 99+% (99.99%-Ag) PURATREM was obtained from Strem Chemicals and used as received. Acetyl acetone, potassium carbonate, 1-bromohexane, hydrazine monohydrate and solvents were purchased from Sigma-Aldrich and used as received without further purification. Acetone was dried over copper sulfate and vacuum distilled. PAO4, a poly-α-olefin oil, was supplied by Ashland and fully formulated military grade (15W40) engine oil was supplied by U.S. Army Tank-Automotive and Armaments Command (TACOM) and used as model base fluids. All deuterated solvents (99+ atom % D) were purchased from Cambridge Isotope Laboratories and used as received. The 52100 steel bar stock was cut into 1 cm×1 cm squares and polished to ~10 nm roughness as measured by atomic force microscope (AFM). Elemental analyses were performed by Galbraith Laboratory, Knoxville, Tenn. (USA). NMR spectra were recorded on a Varian UNITY Inova™ 500 (FT, 500 MHz, $^1$H; 125 MHz, $^{13}$C) instrument. Chemical shifts (δ) for $^1$H and $^{13}$C spectra are referenced using internal solvent resonances. FTIR spectra (4000-700 cm$^{-1}$) were recorded on a Bruker Tensor 37 FTIR equipped with a Mid-IR detector for use between 4000-700 cm$^{-1}$. An AmaZon SL ion trap instrument (Bruker) equipped with an ESI/API Ion Max source was used for mass spectrometry. Instrumental tuning was performed by direct infusion of freshly prepared dichloromethane solution (1 nM) of 1 into a continuous flow of methanol from a solvent delivery system (200 μL min$^{-1}$). Working parameters were set as follows: spray voltage, 3.5 kV; capillary voltage, 15 V; capillary temperature, 200° C.; tube lens, 65 V. Samples were analyzed in flow injection mode using a six-port valve equipped with a 2 μL sample loop. Mass spectra were recorded in full scan analysis mode in the range 0-1500 m/z. Thermogravimetric analysis (TGA) was performed on a TA Q50 ultramicro balance instrument (ramp rate=5° C. min$^{-1}$ and under a $N_2$ flow rate of 90 mL min$^{-1}$ at atmospheric pressure. Films of silver complex 1 were thermolyzed on 52100 stainless steel substrates at 350° C. for 1 min. Film chemical compositions were assessed with an Omicron ESCA Al Kα probe X-ray photoelectron spectrometer (XPS) under high vacuum (<10$^{-8}$ Torr). Ag film phase purity was analyzed by glancing angle/incidence X-ray diffraction (GXRD; angle of incidence α=0.3°) θ-2θ scans on a computer-interfaced Rigaku ATX-G X-ray diffractometer using Ni-filtered Cu Kα radiation.

Synthesis of 3,5-dimethyl-4-n-hexyl-pyrazole ($L^{HPz}$)

Acetylacetone (20.64 mL, 200 mmol) was added drop wise via addition funnel to a stirring solution of oven-dried $K_2CO_3$ (25.7 g, 186 mmol) in acetone (120 mL; distilled from $CuSO_4$). Next, n-hexylbromide (35.27 mL, 246 mmol) was added dropwise via addition funnel. The reaction was refluxed overnight, then cooled and concentrated to dryness. The residue was then dissolved in $Et_2O$ (200 mL) and filtered to remove solids, and the filtrate was concentrated to dryness to give 37.10 g of dark yellow liquid. Impurities of n-hexylbromide and acetylacetone were distilled off at 35° C. and 30 mtorr, and the product was purified by silica gel column chromatography, eluting with ethyl acetate:hexane (1:8) to give 14.28 g of 3-hexyl-2,4-pentanedione as a light-yellow liquid (42% yield). A solution of $N_2H_4 \cdot H_2O$ (3.26 mL, 66.7 mmol) in MeOH (20 mL) was slowly added (over 20 min) via cannula transfer to a 0° C. solution of 3-hexyl-2,4-pentanedione (12.30 g, 66.7 mmol) in MeOH (50 mL). The mixture was stirred for 12 h at room temperature, and then refluxed for 4 hrs. The solvent was then removed in vacuo and the light yellow liquid is dried to give 11.00 g (93% yield) of 3,5-dimethyl-4-n-hexyl-pyrazole ($L^{HPz}$). $^1$H NMR ($CDCl_3$): δ=3.45 (s, 1H, —NH—), 2.30 (t, 2H, —$CCH_2CH_2$—), 1.99 (s, 3H, —$CH_3$), 1.82 (s, 3H, —$CH_3$), 1.44 (q, 2H, —$CH_2CH_2CH_2$—), 1.26 (m, 6H, alkyl chain), 0.86 (t, 3H, —$CH_2CH_3$) ppm. $^{13}$C NMR ($CDCl_3$): δ=115.94, 31.89, 30.75, 29.18, 23.17, 22.81, 14.23, 11.03 ppm. ESI-MS (p.i., $CH_2Cl_2$/MeOH 95:5, m/z, I %)=181.03 m/z $[LH]^+$.

Synthesis of Ag(3,5-dimethyl-4-n-hexyl-pyrazole) (1)

Solid $Ag_2O$ (7.16 g, 30.9 mmol) was added to a solution of $L^{HPz}$ (11.03 g, 61.2 mmol) in anhydrous MeOH (100 mL) while stirring. Then MeOH (35 mL) was added and the mixture stirred at room temperature for 24 h, then refluxed for 6 h, followed by further room temperature stirring for 18 h. Solvent was then evaporated under reduced pressure, and the crude product dissolved in hexanes and filtered to remove insoluble particles. The filtrate was then concentrated and the product recrystallized from hexanes to give Ag(3,5-dimethyl-4-n-hexyl-pyrazole) (1) as a white powder (77% yield). $^1$H NMR (CDCl$_3$): δ=2.34 (t, 6H, —CCH$_2$CH$_2$—), 2.04 (s, 18H, —CH$_3$), 1.44 (qu, 6H, —CH$_2$CH$_2$CH$_2$—), 1.31 (m, 18H, alkyl chain), 0.90 (t, 9H, —CH$_2$CH$_3$) ppm. $^{13}$C NMR (CDCl$_3$): δ=172.65, 147.33, 113.78, 110.15, 32.00, 31.28, 29.38, 24.07, 22.92, 14.30, 12.80 ppm. Elem. Anal. Calcd.: Ag, 37.56%; C, 46.01%; H, 6.67%; N, 9.76%; found: Ag, 38.02%; C, 45.52%; H, 6.59%; N, 9.87%. ESI-MS (p.i., CH$_2$Cl$_2$/MeOH 95:5, m/z)=181.03 m/z 467.20 m/z [AgL$_2$H]$^+$; 755.26 m/z [Ag$_2$L$_3$H]$^+$.

Single Crystal X-Ray Structures.

Single-crystal data were collected with a Bruker Smart APEXII area detector diffractometer (Mo Kα; λ=0.71073 Å). Cell parameters were refined from the observed setting angles and detector positions of selected strong reflections. Intensities were integrated from several series of exposure frames that covered the sphere of reciprocal space. A multiscan absorption correction was applied to the data using the program SADABS. The structures were solved by direct methods and refined with full-matrix least-squares (SHELXL-97), using the Wingx software package. Graphical material was prepared with the Mercury 3.0 program.

Tribology Experiments

Silver complex 1 was combined with PAO4 and 15W40 military-grade engine oil (FF oil). The complex was dissolved in the minimal amount of hexane (1 mL per 1 g silver complex) and then added to the oil to achieve complex concentrations of 1.0, 2.5 and 5.0 wt %. Before testing, the oil-silver complex mixtures were stirred with a magnetic stir bar for 30 minutes to ensure a homogeneous dispersion.

Lubricated Sliding Interaction of Stationary Pin-On-Rotating Disk.

Figure 2:
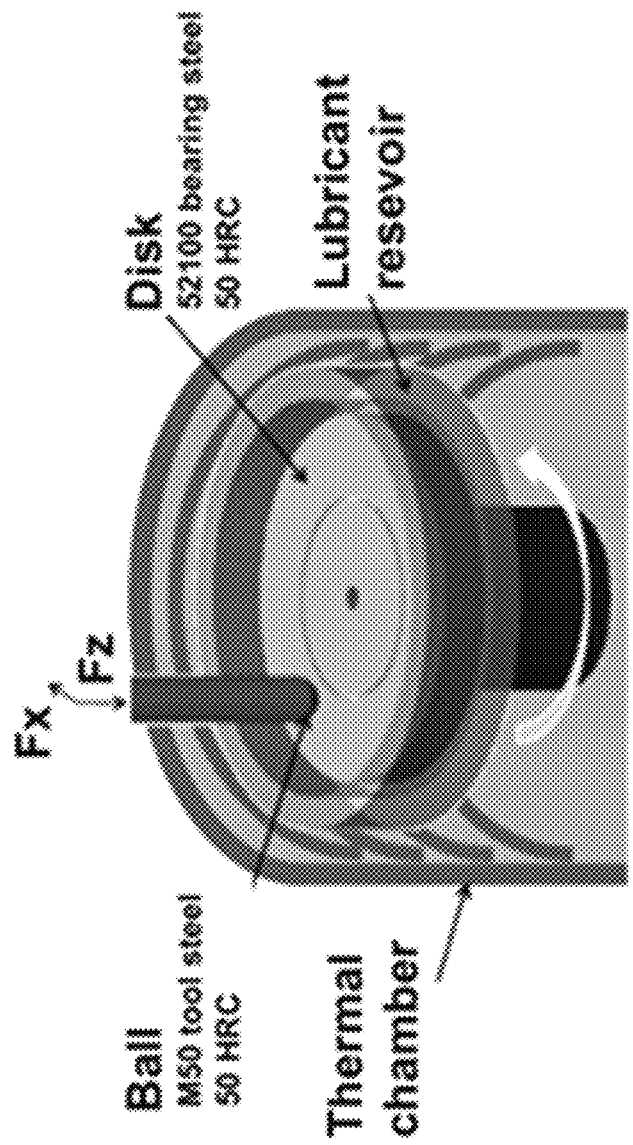
FIG. 2 shows a schematic of a temperature-controlled CETR UMT-2 ball-on-disk tribometer with heating chamber.

A schematic of a pin-on-disk tribometer (CETR UMT-2 tribometer) used in this study is shown in FIG. 2. Table 1 outlines the experimental conditions used in this study. A ball bearing made of M50 bearing steel with 62 HRC hardness and a diameter of 4 mm is used to apply a vertical load to a 52100 steel disk with 50 HRC hardness and a diameter to 3" as the disk rotates. The surface of the disk is coated with a 2 mL solution of 1 in the desired base oil. The sliding test conditions for all the experiments were: Normal load=25 N, sliding velocity=200 rpm. In the temperature ramp experiments, the temperature is increased from 180-350° C. over 30 min in order to detect any change in frictional characteristics as the oil degrades, and partially evaporates, and once the metallic Ag is deposited. The maximum contact pressure and film thickness of the tests were computationally predicted to be 2.15 GPa and 0.15 μm, respectively, indicating that the these tests take place in the boundary lubrication regime.

TABLE 1

Tribometer evaluations conditions and sample formulations

| Test Parameter | Value |
| --- | --- |
| Applied load (N) | 25 |
| Hertzian Contact Pressure (GPa) | 2.15 |
| Disk rotation speed (rpm) | 200 |
| Radial location of contact (mm) | 20 |
| Sliding contact speed (m/s) | 0.42 |
| Total sliding distance (m) | 754 |
| Base oil | PAO4 FF mil-grade 15W-40 |
| Ag additive concentration (wt %) | 0.0, 1.0, 2.5, 5.0 |
| Temperature range (° C.) | 180-350 |
| Rate of temperature change (° C./s) | 0.1 |
| Test duration (min) | 30 |

Wear Analysis by White Light Interferometry

After friction tests were completed, the disks were sonicated in a hexane bath to remove oil residue. The volume of the wear scar was measured using a Zygo NewView 7100 white light interferometer. The wear volume and material buildup around the wear scar were used to calculate the wear rate, which is defined as the volume removed per unit load per sliding distance. Each additive concentration in oil was tested twice for friction and wear performance. Energy-dispersive X-ray spectroscopy (EDS) on Hitachi S4800-II and Hitachi SU8030 Scanning Electron Microscopes (SEMs) was used to examine the morphology of the disk surface and deposited silver content.

Results and Discussion

Silver-Organic Additive Synthesis and Characterization

Figure 3:
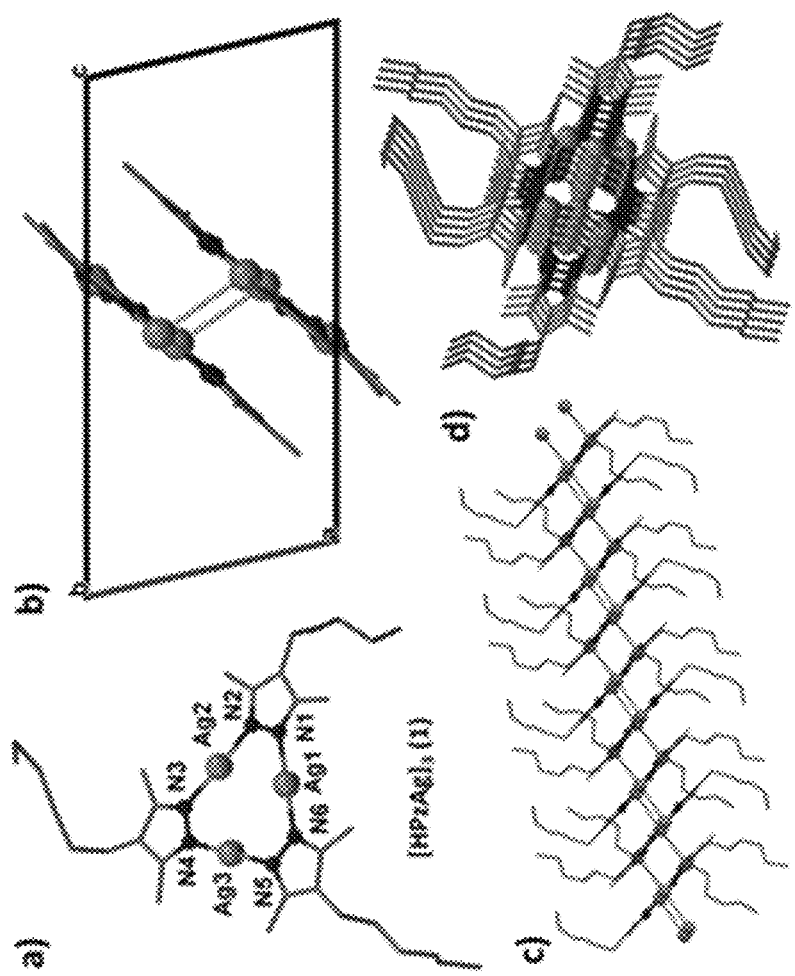
FIG. 3 shows: (a) Crystal structure of organo-silver lubricant additive 1 (1). Hydrogen atoms are omitted for clarity. Selected bond distances (Å) and angles (°) are: Ag1-N1=2.077, Ag1-Ag2=3.393, Ag1-N1-N2=118.56, N6-Ag1-N1=178.49; (b) Molecular packing in organo-silver lubricant additive 1. Hydrocarbon chains are omitted for clarity. Intermolecular Ag..Ag distance=3.216 Å. (c) side view and (d) top view of crystal packing.
Figure 12:
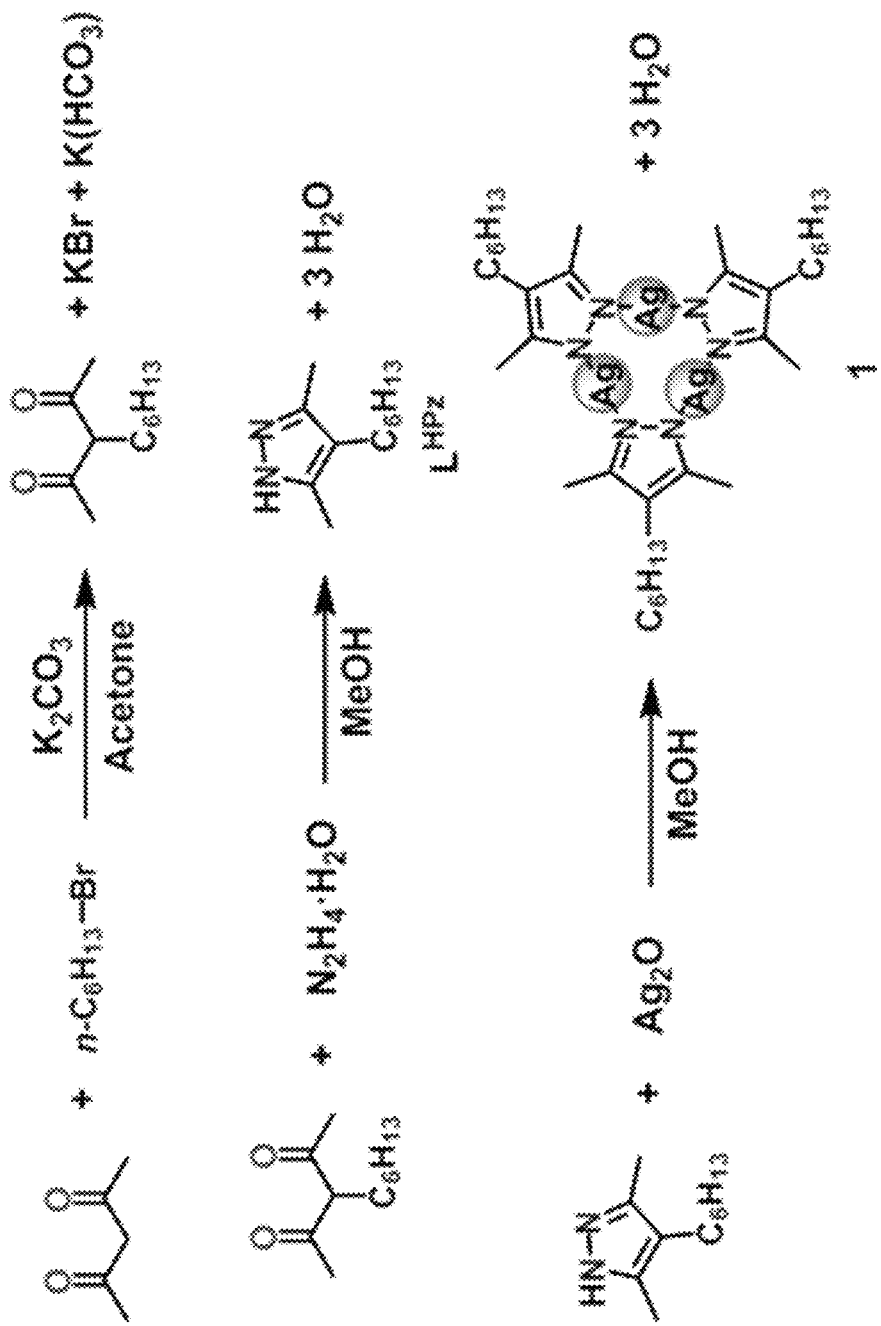
FIG. 12 shows a synthesis of organo-silver lubricant additive 1.
Figure 13:
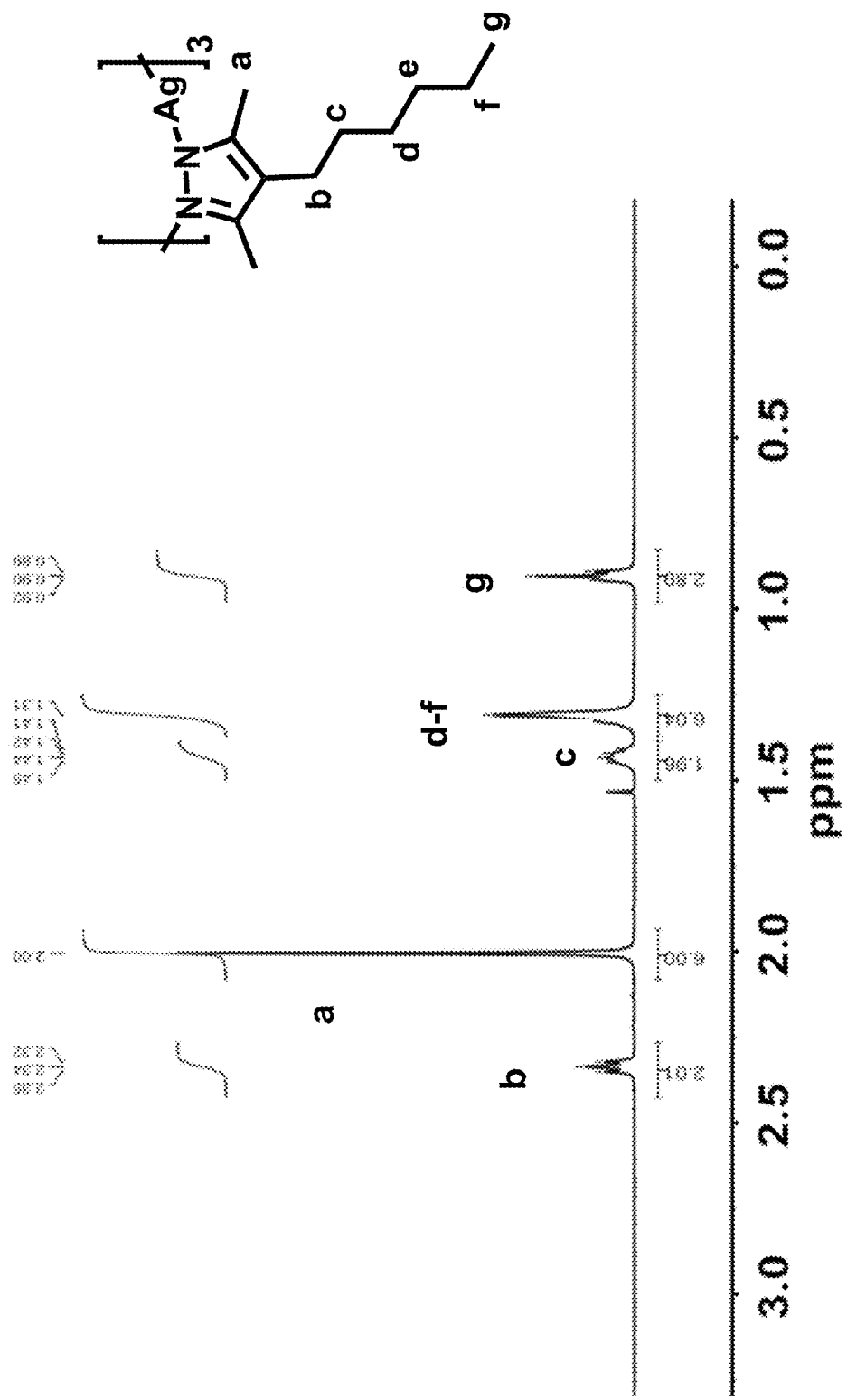
FIG. 13 shows a 1H NMR spectrum of organo-silver lubricant additive 1.

The synthesis of 1 is outlined in FIG. 12. The ligand is prepared by attaching an n-hexyl chain to acetylacetone via an S$_N$2 mechanism. Hydrazine is then used to close the nitrogen heterocycle (L$^{HPz}$) under refluxing conditions. L$^{HPz}$ is reacted with silver oxide at 0° C. and then warmed to a room temperature to afford silver complex 1 in 77% yield as white powder. Compound 1 is fully characterized by spectroscopic ($^1$H NMR) and analytical methods, as well as by single-crystal XRD. Single crystal X-ray diffraction crystallographic results reveal that the pyrazole ligands and silver atoms in complex 1 form a ring structure, with each silver atom coordinated to two nitrogen centers (FIG. 3a). The intramolecular Ag...Ag distance of 3.45(9) Å indicates that a significant intramolecular argentophilic interaction is unlikely. However, a more significant intermolecular argentophilic interaction with a bond distance of 3.216 Å is observed, leading to a staggered ladder stacking motif between adjacent molecules in the crystal structure (FIG. 3b).

Figure 4:
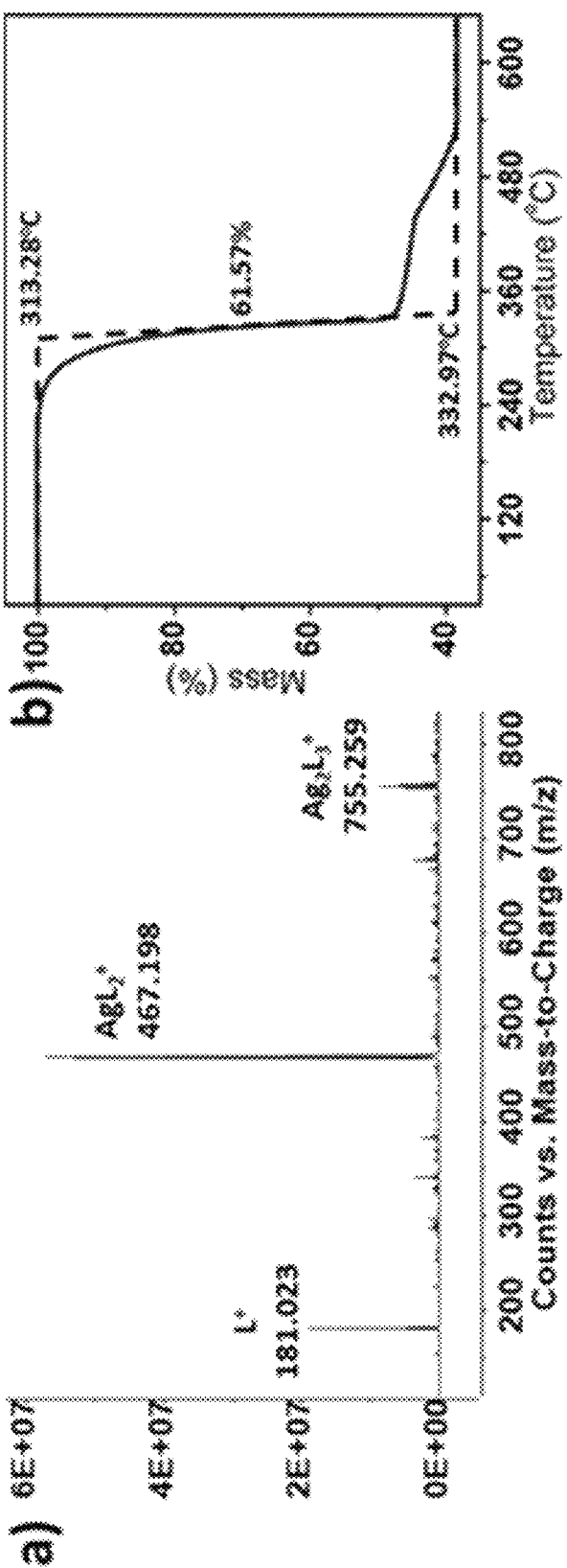
FIG. 4 shows: (a) ESI-MS of organo-silver lubricant additive 1 dissolved in dichloromethane. Fragmentation shows possible decomposition pathways for organo-silver lubricant additive 1. (b) Thermogravimetric analysis trace for organo-silver lubricant additive 1. Organo-silver lubricant additive 1 thermolyzes above 300° C. and creates a film that is almost entirely metallic silver (93.6%).
Figure 8:
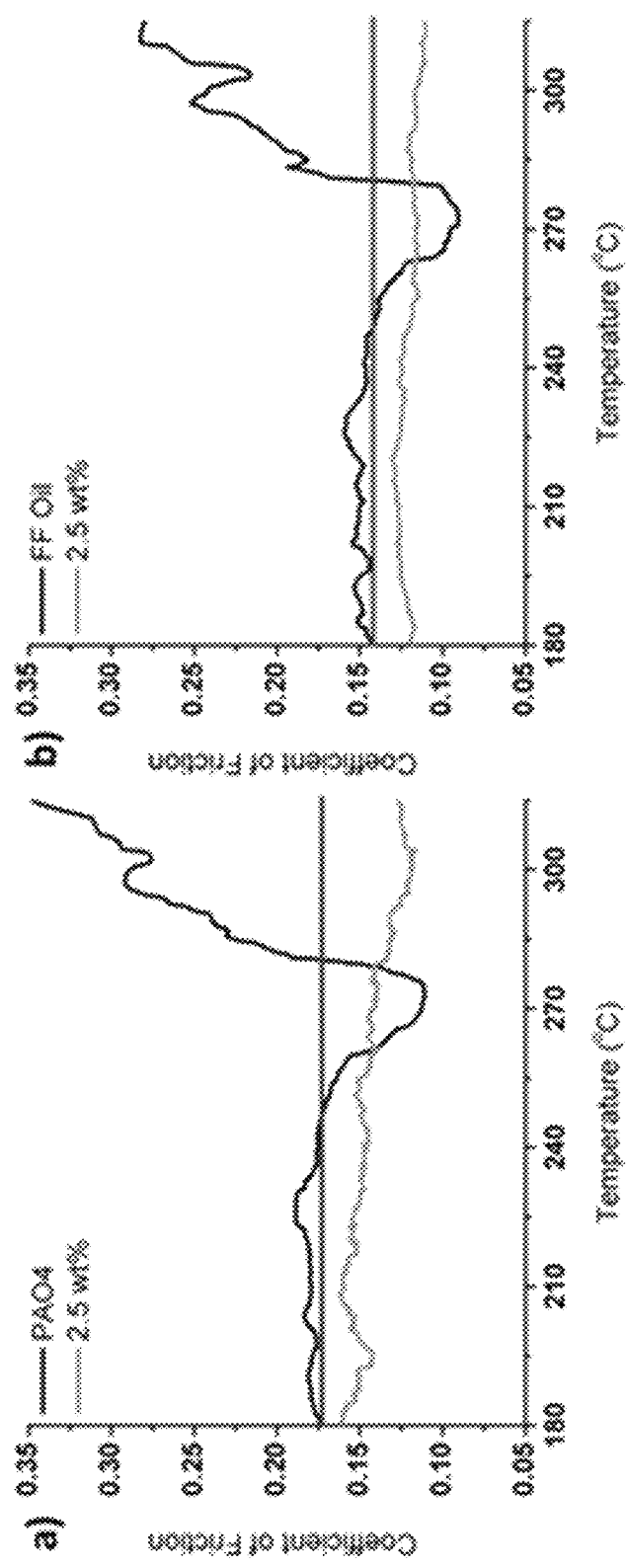
FIG. 8 shows ball-on-disk tribometer tests with lubricated contact. Oil mixture is a 2.5 wt % loading of organo-silver lubricant additive 1 in (a) PAO4 and (b) FF oil. Temperature is ramped from 180 to 350° C. over 30 minutes. The flat line from each y-axis shows baseline friction for pure PAO and FF oil.

ESI-MS provides useful information on molecular aggregation and fragmentation, which in turn is likely to influence thermolysis pathways. [AgL$_2$]$^+$ and [Ag$_2$L$_3$]$^+$ signals are identified in the ESI mass spectrum (FIG. 4a). The occurrence of these fragments under gentle ionization conditions suggest the lability of the trimer complex which may represent the initial steps in silver film deposition. Atmospheric pressure thermogravimetric analysis (TGA) of silver complex 1 was performed under N$_2$ to evaluate the temperature at which thermolysis begins. It was found that complex 1 starts to thermolyze at 300° C., which is a more desirable thermolysis temperature than the 200° C. at which the Gen-II and Gen-III additives thermolyze. Ramping temperature experiments (FIG. 8) have shown that the PAO4 and 15W40 motor oil used as base oils in these experiments starts to decompose at 275° C. At the completion of a TGA scan, 38.5% of the original mass remains (FIG. 4b). Elemental analysis shows that complex 1 is 38.02 wt % silver, which means that a majority of the residue remaining after thermolysis (38.5%) is silver metal.

Solubility of Complex 1 in Base Oil

Figure 5:
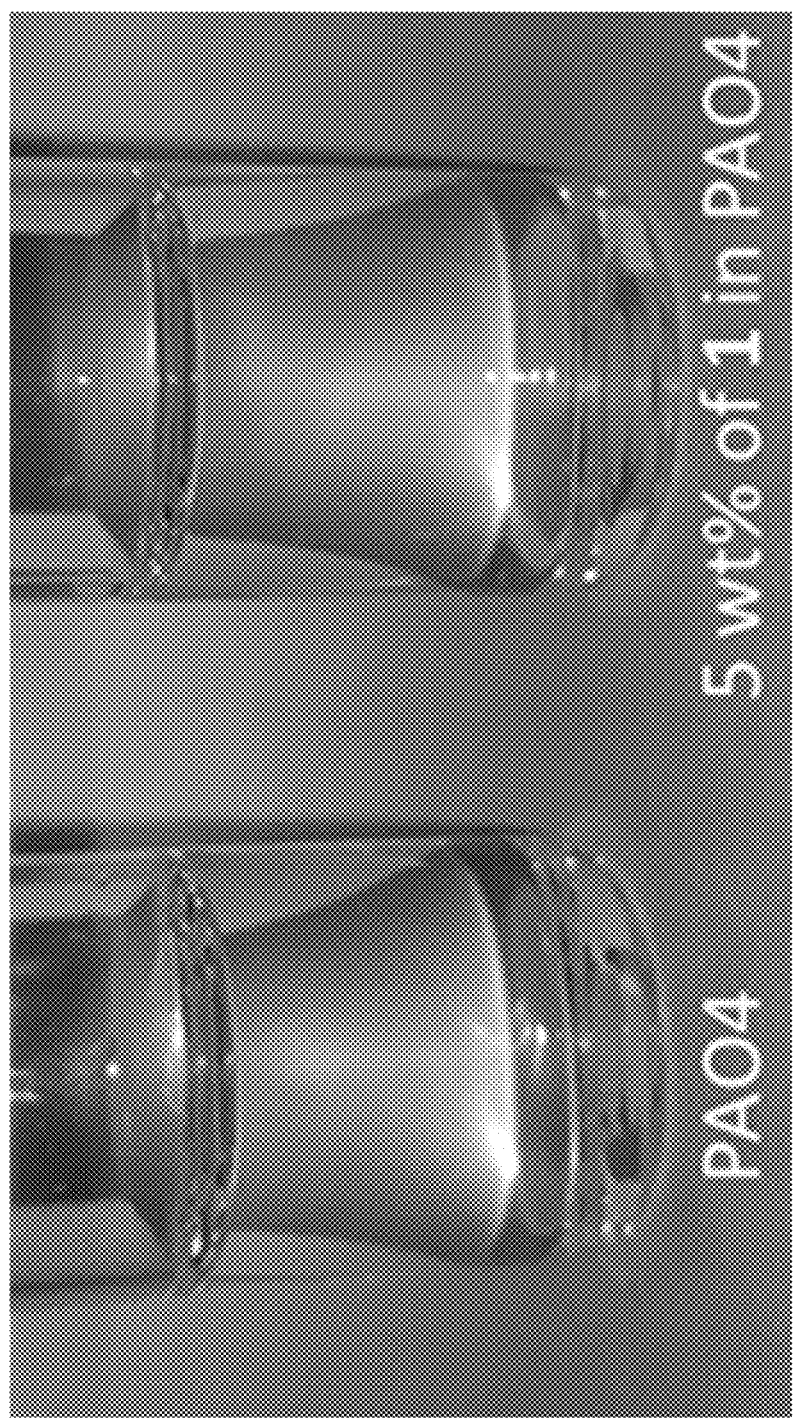
FIG. 5 shows a vial of pure PAO4 (left) and a 5 wt % solution of organo-silver lubricant additive 1 in PAO4 (right), which shows a light yellow tint and no insoluble material (colour not shown in figures).

Solubility in base oil is an important property for tribologically promising high temperature additives, and is something that challenged previous generations of silver-organic additives. The aforementioned Gen-III additive (FIG. 1c) was highly promising in that it was S- and P-free and undergoes decomposition at high temperature to form metallic silver films, however it requires very large loadings and forms a cloudy, opaque mixture in oil. In contrast, gentle heating of a 5 wt % loading 1 at 40° C. in PAO4 yields a homogeneous solution (FIG. 5).

Silver Complex 1 Thermolysis

Figure 6:
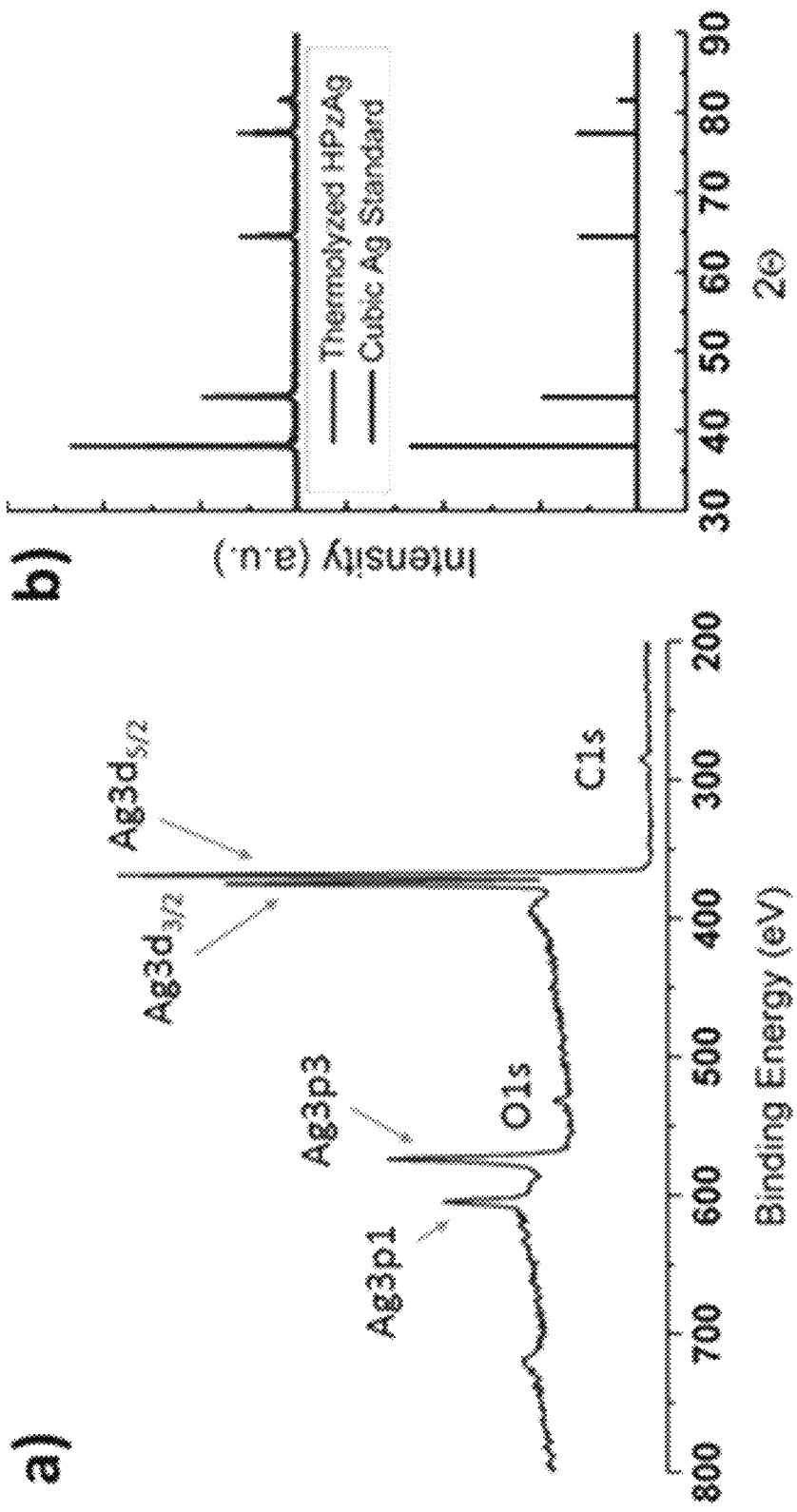
FIG. 6 shows Ag film deposited on 52100 steel substrate after thermolysis of organo-silver lubricant additive 1 at 350° C. for 10 min (a) XPS spectrum, (b) GIXRD diffractogram (θ-2θ) (b top). Peak positions and relative intensities for the powder pattern of cubic phase Ag (PDF 04-0783) (b bottom).

Powder X-ray diffraction (PXRD), X-ray photoelectron spectroscopy (XPS) and elemental analysis (EA) were performed to characterize the thermolysis residue. Elemental analysis reveals that the composition of the residue is: Ag, 93.6%; C, <0.5%; H, <0.5%; N<0.5%. The remaining ~4.5% is attributed to O, which presumably arises from $Ag_2O$ formation during thermolysis. The purity of the Ag film was also investigated by XPS (FIG. 6a) and glancing angle/incidence X-ray diffraction (GIXRD, FIG. 6b). The XPS spectrum exhibits characteristic metallic Ag $3d_{5/2}$ and $3d_{3/2}$ signatures, with no detectable traces of contaminants, while the GIXRD reveals cubic metallic Ag (PDF 04-0783).

Evaluation of 1 as a Lubricant Additive. Friction and Wear Measurements

Silver complex 1 was added to oil at 0.0, 1.0, 2.5, and 5 wt % loadings. A minimal amount of hexanes was added to aid in solubilizing the complex (1 mL hexanes/g of complex) before mixing with oil. The oils used are PAO4, a base oil with no additives, and a military-grade 15W40 oil, which is fully formulated (FF) but contains no silver-containing additives (confirmed by elemental analysis). Adding silver complex 1 to either oil creates a cloudy suspension at room temperature that dissolves fully with heating to 40° C. and magnetic stirring.

Figure 7:
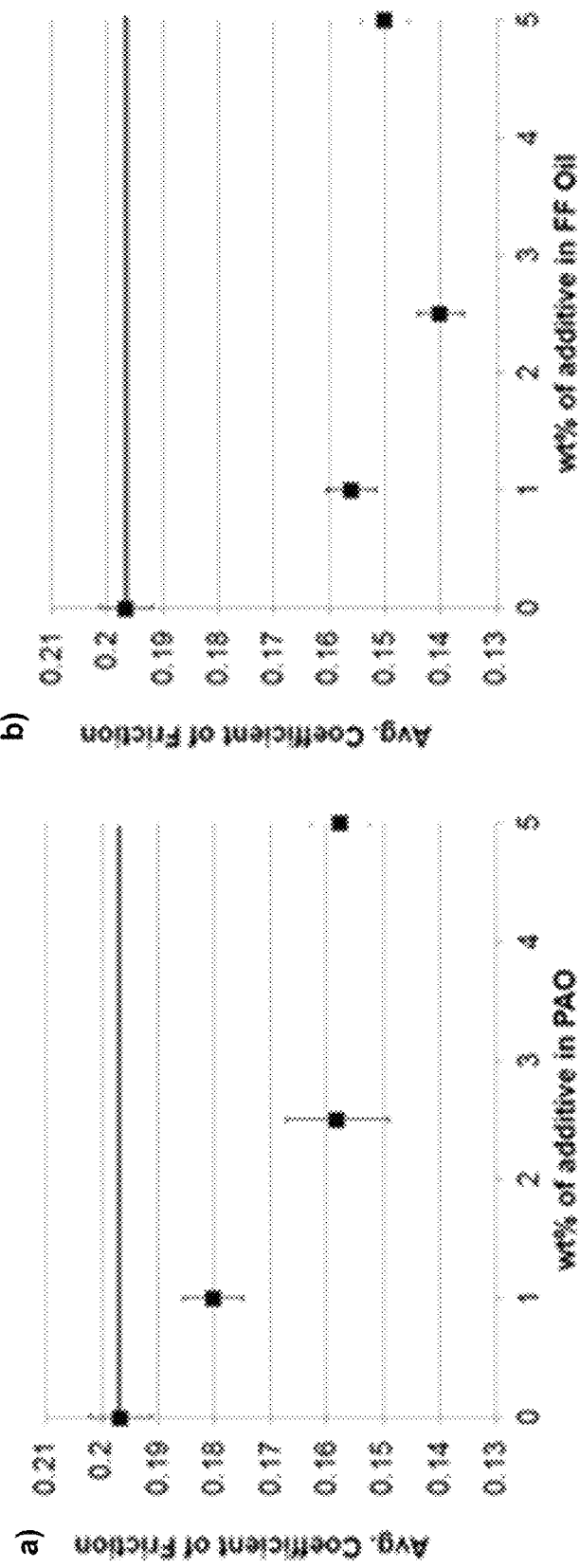
FIG. 7 shows ball-on-disk measurements of friction with increasing loadings of organo-silver lubricant additive 1 in (a) PAO and (b) 15W40. Each data point is the average of a temperature ramp experiment from 180° C. to 350° C. over 30 mins. The flat line from each y-axis shows baseline friction for pure PAO and FF oil.

The effects of differing concentrations of 1 in PAO4 and 15W40 were determined by pin-on-disk tribometry (FIG. 7). Friction reduction is preferred, but not absolutely necessary for high temperature additives. Pin-on-disk tribometry is used to ensure that 1 does not have detrimental effects on the coefficient of friction (COF). FIG. 7 shows that 1.0, 2.5 and 5 wt % loadings of 1 all tend to reduce friction. A 2.5 wt % loading of 1 reduces friction by 20% in PAO4 and by 30% in 15W40. Loadings greater than 2.5 wt % do not decrease friction further. A similar friction-additive concentration relationship is also observed in previous generations of the silver additives. The ball-on-disk friction tests shown in FIG. 8 were performed while ramping temperature from 180 to 350° C. over 30 min. These plots show a steep increase in COF that begins around 275° C. for both base oils, PAO4 and 15W40. Initial COF measurements for base oil range between 0.15 and 0.20 for PAO4 and between 0.10 and 0.15 for 15W40, while the final measurements reach 0.30. Note that 15W40 has lower initial COFs because the additive package includes friction modifiers. Both oils exhibit a similar spike in COF at ~275° C. which can be explained by degradation of oil at high temperature. However, when a 2.5 wt % loading of 1 is used in either base oil, remarkably, the COF does not increase as the oil begins to degrade above ~275° C. The transition from oil as the primary lubricant to metallic silver as primary lubricant is clearly seamless.

Surface Analysis

Figure 9:
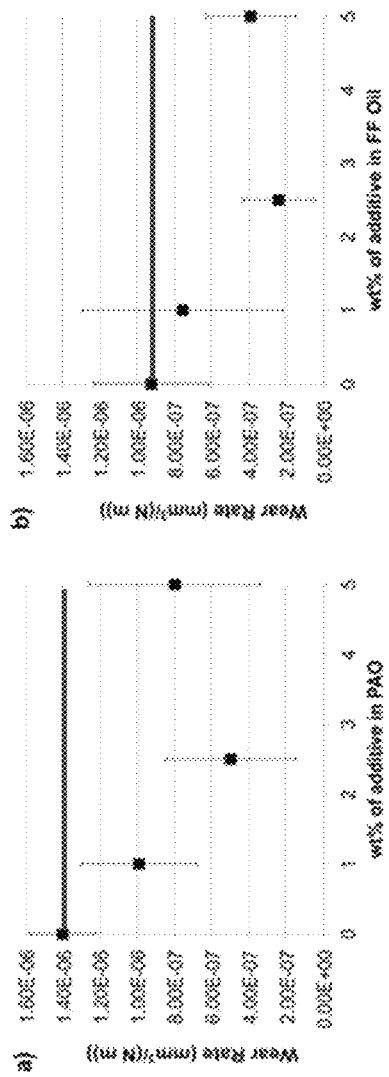
FIG. 9 shows wear rate measurements for the temperature-ramped pin-on-disk tribometer substrates for organo-silver lubricant additive 1 in (a) PAO4 and (b) fully formulated oil. White light interferometry is used to measure the volume of the wear scar at 12 positions, and the volumes for each wear scar are then averaged. The flat line from each y-axis shows baseline friction for pure PAO and FF oil.

The disks used in the temperature ramp tests (FIG. 8) were next analyzed by white light interferometry to determine the volume of the wear scars and the material buildup outside of the scar. The volume of material removed was normalized for load and the distance traveled during the test. It is found that a 2.5 wt % loading of additive 1 reduces wear by 60% in PAO4 and by 70% in 15W40 (FIG. 9). The trend in wear rate is similar to the trend in COF (FIG. 7), with a 2.5 wt % loading producing the lowest amounts of wear. The Gen-III additive produces comparable friction and wear results at a 20 wt % loading. It is hypothesized that the increase in efficiency of additive 1 is attributable to the increased number of silver atoms/molecule and improved solubility in oil, which enables better dispersion of the additive in base oil.

Figure 10:
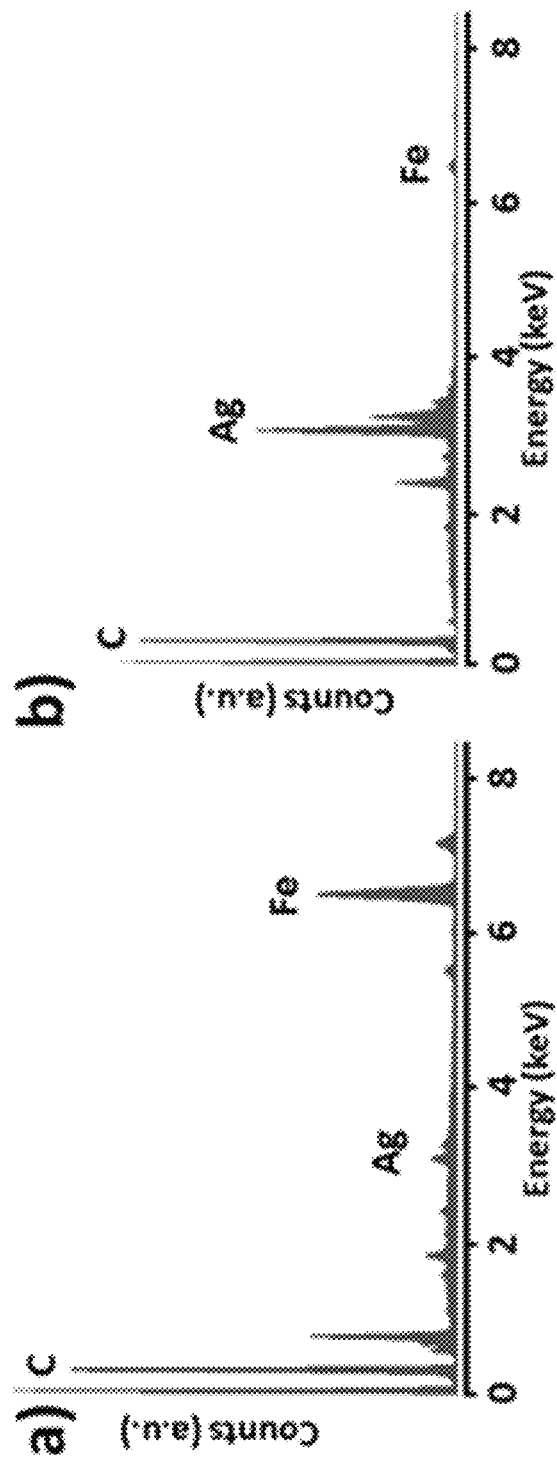
FIG. 10 shows energy dispersive spectroscopy (EDS) of the (a) outside of the post-test wear scar and (b) the inside of the wear scar.

Scanning electron microscopy (SEM) coupled with energy-dispersive X-ray spectroscopy (EDS) was used to analyze the elemental composition of the area in and around wear scars of the steel substrates used in the friction and wear tests. FIG. 10 shows EDS spectra for areas outside and inside the wear scar after pin-on-disk tests were carried out with a 2.5 wt % loading of the additive in PAO4.

EDS shows a much lower concentration of silver outside the wear scar, indicating that thermolysis and subsequent silver deposition only occur where needed. It is likely that heat and pressure from the contacting surfaces promotes decomposition of the silver additive. Neither the PAO4 nor 15W40 fully formulated motor oil used have additives containing silver, therefore it can be concluded that the silver particles deposited on the metal surface result from thermolysis of additive 1.

Figure 11:
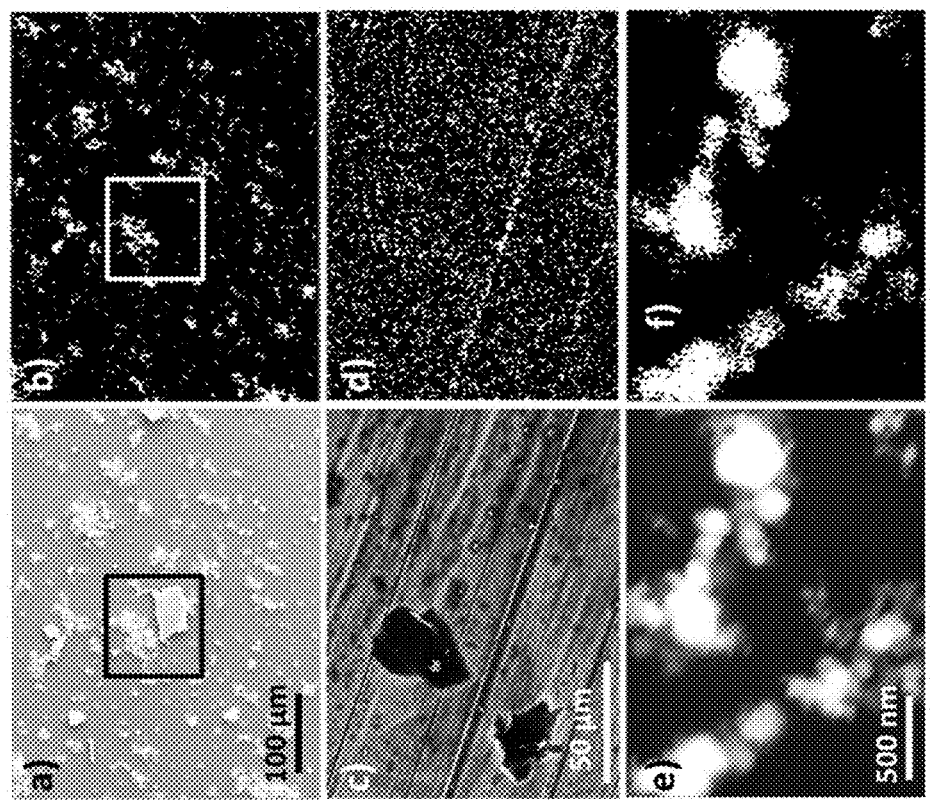
FIG. 11 shows SEM images and 2D EDS maps of (a, b) a silver agglomeration next to a piece of wear debris, (c, d) area inside a wear scar with deep scars from asperity contact, and (e, f) agglomerations of silver nanoparticles inside a wear scar.

SEM was also used to investigate the size of the particles formed by thermolysis (FIG. 11). The silver is primarily deposited in the form of microparticles in the wear scar, which appear to be the result of silver nanoparticle agglomerations ranging from 10-100 μm in diameter. The box in the center of FIG. 11a highlights an agglomeration of silver next to a piece of wear debris. 2D elemental mapping of silver (FIG. 11b) shows that the wear debris contains no silver. FIG. 11c shows an image taken from the inside of a wear scar, with deep tracks resulting from asperity contacts. 2D mapping of this region (FIG. 11d) shows a higher concentration of silver inside these deep scars, which demonstrates that the silver is primarily deposited where it is needed as a result of high temperature and pressure. FIGS. 11e and f show a higher magnification image and 2D mapping of agglomerated silver nanoparticles inside the wear scar.

Without wishing to be bound by theory, the mechanism by which complex 1 functions to reduce friction and wear is likely due to its nanometer size, chemical structure, thermolytic reactivity and material properties. This organosilver complex undergoes thermolysis at elevated temperature and pressure to deposit Ag nanoparticles, whose softness prevents the particles from acting as abrasives on the interface surfaces. This is a similar mechanism of action to previously reported lubricant anti-wear additives, such as zinc dialkyldithiophosphates (ZDDP, ZDTP), which are believed to supplement base oil by forming a thin film on the interface surfaces and protecting against wear in the boundary lubrication regime, where surface asperities in the interface come into contact. Another proposed mechanism involves physisorption of the anti-wear additives onto the metal surfaces, rather than a chemical reaction which produces polymeric reaction products which act to reduce friction. DDP-coated silver nanoparticles have demonstrated reduced electrical resistance at the point of contact through electrical contact resistance measurements. This performance was attributed to a melting and welding of the silver under boundary lubrication, thus promoting good conductivity. Silver nanoparticles studied as anti-friction and anti-wear additives have been shown by XPS and EDS analysis to deposit a relatively large amount of silver in the pure metallic form, indicating that the nanoparticles used as additives do not chemically react with steel surfaces, but instead provide anti-wear properties through formation of a boundary film with low shear stress. Additionally, $MoS_2$ nanoparticles have been demonstrated by in situ transmission electron microscopy (TEM) to provide surface protection through mechanical behavior by deforming, rolling, and shearing through the point of contact rather than by chemical reaction. The new metallic precursor complexes reported here yield a product (e.g. silver precursors produce silver metal) that functions similarly to $MoS_2$ yet is even more inert and is therefore believed not to undergo chemical reaction with the surface, but to be physisorbed via weak interactions. Plastic deformation and material removal are both observed in the wear scar (FIG. 9), and small amounts of silver are found in the wear scar based on EDS analysis (FIG. 11). Without wishing to be bound by theory, the primary mechanism for reducing friction and wear is therefore attributed in one non-limiting embodiment to the properties of silver, particularly its softness and low shear strength. In addition, silver provides a mechanical buffer between the interacting surfaces; the silver particles, as they roll or shear through the contacts, reasonably act as sacrificial surfaces.

Summary

Lubricant additives have been prepared and shown to have beneficial properties in reducing friction and wear. In one non-limiting embodiment, silver-organic additives can be used to deposit metallic silver on a mechanical surface at high thermolytic temperatures, thereby reducing friction and wear at temperatures where base oil degradation occurs. Compound 1 is a non-limiting example of a new generation of lubricant additives that exhibit useful solubility in non-polar base oil. Compound 1 undergoes thermolysis between 313 and 332° C. to produce lubricous silver films. Temperature-ramped ball-on-disk experiments show that 1 significantly reduces friction at temperatures greater than ~275° C., the region where both PAO4 and 15W40 fail to effectively reduce friction. The transition from oil as primary lubricant to metallic silver as primary lubricant is seamless. SEM and EDS analysis show that metallic silver is primarily deposited in wear scars, indicating that high temperature caused by asperity contacts increases the probability of thermolysis for the additive. The metallic silver is deposited in the form of nano/microparticles which act as a protective barrier between the contacting surfaces. Compound 1 is particularly effective at a 2.5 wt % loading with decreased performance when concentration is increased to a 5 wt % loading. These results are an improvement over previous silver-organic additives which required higher loadings to achieve comparable anti-friction and anti-wear performance.

The present inventors have discovered a new class of lubricant additive. The lubricant additives of the present invention are as set out in the claims. When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims." The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

We claim:

1. A mixture comprising:
a lubricant additive having the structure of general formula I:

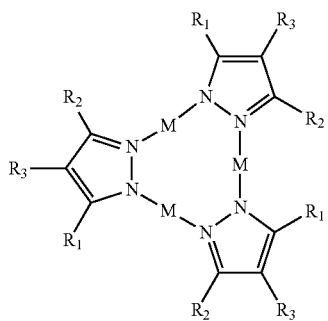

wherein:
M is a metal,
R₁ is hydrogen, alkyl, substituted alkyl, or aryl,
R₂ is hydrogen, alkyl, substituted alkyl, or aryl, and,
R₃ is hydrogen, alkyl, substituted alkyl, or aryl; and oil,
wherein the oil is PAO4 or 15W40 oil.

2. A mixture comprising:
a lubricant additive having the structure of general formula I:

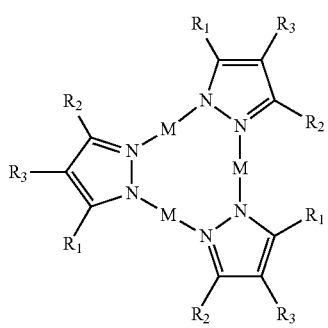

wherein:
M is a metal,
R₁ is hydrogen, alkyl, substituted alkyl, or aryl,
R₂ is hydrogen, alkyl, substituted alkyl, or aryl, and,
R₃ is hydrogen, alkyl, substituted alkyl, or aryl; and oil,
wherein the oil has a viscosity of at least 16.8 mPa·s at 40° C.

3. The mixture of claim 1, wherein M is Ag, Au, Zn or Cu; optionally, wherein M is Ag.

4. The mixture of claim 1, wherein:
R₁ is alkyl,
R₂ is alkyl, and,
R₃ is alkyl.

5. The mixture of claim 1, wherein:
each alkyl is independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms.

6. The mixture of claim 5, wherein each alkyl is independently selected from the group consisting of methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl and eicosyl.

7. The mixture of claim 1, wherein:
each substituted alkyl is independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms substituted with 1, 2, 3, 4, 5, 6, 7, 8, 9, 10, 11, 12, 13, 14, 15, 16, 17, 18, 19, 20 or more substituents, the substituents independently selected from the group consisting of H, aryl, alkenyl, alkynyl, arylalkyl, alkoxy, aryloxy, arylalkoxy, alkoxyalkylaryl, alkylamino, arylamino, NH₂, OH, CN, NO₂, OCF₃, CF₃, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR₄, SOR₄, SO₂R₄, CO₂R₄, COR₄, CONR₄R₄, CSNR₄R₄ and SOnNR₄R₄, where n is zero, one or two, wherein R₄ is alkyl or substituted alkyl.

8. The mixture of claim 1, wherein:
R₁ and R₂ are each independently any one of CH₃, CF₃, t-Bu or CH₂CH₃.

9. The mixture of claim 8, wherein R₁ and R₂ are the same.

10. The mixture of claim 1, wherein R₁ and R₂ are CH₃.

11. The mixture of claim 1, wherein:
R₃ is H or (CH₂)ₙCH₃, wherein n is 0, 1, 2, 3, 4, 5, 6, 7, 8, 9, 10, 11, 12, 13, 14, 15, 16, 17, 18, 19 or 20.

12. The mixture of claim 1, wherein:
R₃ is (CH₂)₅CH₃.

13. The mixture of claim 1, wherein the lubricant additive is not:

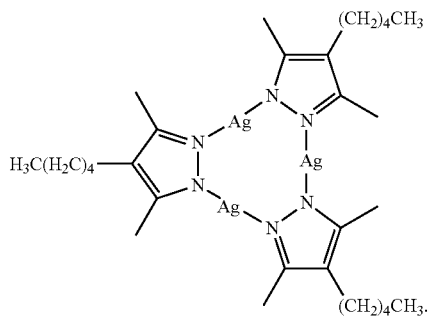

14. The mixture of claim 1, wherein the lubricant additive is not:

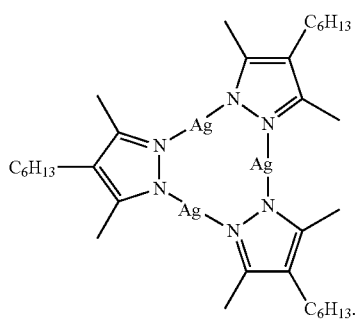

15. The mixture of claim 2, wherein M is Ag, Au, Zn or Cu; optionally, wherein M is Ag.

16. The mixture of claim 2, wherein:
$R_1$ is alkyl,
$R_2$ is alkyl, and,
$R_3$ is alkyl.

17. The mixture of claim 2, wherein:
each alkyl is independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms.

18. The mixture of claim 17, wherein each alkyl is independently selected from the group consisting of methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl and eicosyl.

19. The mixture of claim 2, wherein:
each substituted alkyl is independently selected from the group consisting of straight-chain or branched-chain hydrocarbons having 1, 2, 3, 4, 5, 6, 7, 8, 9, 10, 11, 12, 13, 14, 15, 16, 17, 18, 19 or 20 carbon atoms substituted with 1, 2, 3, 4, 5, 6, 7, 8, 9, 10, 11, 12, 13, 14, 15, 16, 17, 18, 19, 20 or more substituents, the substituents independently selected from the group consisting of H, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide,pyrazolo, oxazole, isoxazole, pyridinyl, pyrimidinyl, quinoline, isoquinoline, $SR_4$, $SOR_4$, $SO_2R_4$, $CO_2R_4$, $COR_4$, $CONR_4R_4$, $CSNR_4R_4$ and $SOnNR_4R_4$, where n is zero, one or two, wherein $R_4$ is alkyl or substituted alkyl.

20. The mixture of claim 2, wherein:
$R_1$ and $R_2$ are each independently any one of $CH_3$, $CF_3$, t-Bu or $CH_2CH_3$.

21. The mixture of claim 20, wherein $R_1$ and $R_2$ are the same.

22. The mixture of claim 2, wherein $R_1$ and $R_2$ are $CH_3$.

23. The mixture of claim 2, wherein:
$R_3$ is H or $(CH_2)_nCH_3$, wherein n is 0, 1, 2, 3, 4, 5, 6, 7, 8, 9, 10, 11, 12, 13, 14, 15, 16, 17, 18, 19 or 20.

24. The mixture of claim 2, wherein:
$R_3$ is $(CH_2)_5CH_3$.

25. The mixture of claim 2, wherein the lubricant additive is not:

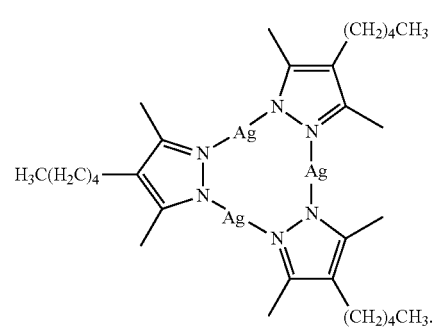

26. The mixture of claim 2, wherein the lubricant additive is not:

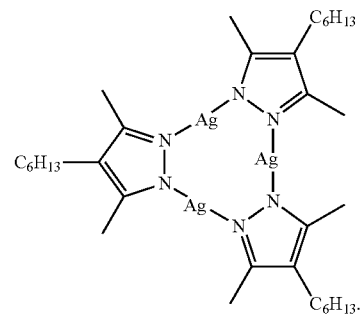

27. The mixture of claim 2, wherein the oil is PAO4 or 15W40 oil.

* * * * *